(12) United States Patent
Wollan et al.

(10) Patent No.: US 8,361,479 B2
(45) Date of Patent: Jan. 29, 2013

(54) PROMISCUOUS PAP CD4 T CELL EPITOPES

(75) Inventors: Jami B. Wollan, Mountlake Terrace, WA (US); Lori A. Jones, Seattle, WA (US)

(73) Assignee: Dendreon Corporation, Seattle, WA (US)

( * ) Notice: Subject to any disclaimer, the term of this patent is extended or adjusted under 35 U.S.C. 154(b) by 1516 days.

(21) Appl. No.: 11/836,653

(22) Filed: Aug. 9, 2007

(65) Prior Publication Data

US 2008/0286293 A1 Nov. 20, 2008

Related U.S. Application Data

(60) Provisional application No. 60/837,053, filed on Aug. 11, 2006.

(51) Int. Cl.
*A61K 39/00* (2006.01)
*A61K 38/00* (2006.01)
*A61K 38/04* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl. ............. 424/185.1; 424/192.1; 514/1.1; 530/300; 530/326

(58) Field of Classification Search ............ None
See application file for complete search history.

(56) References Cited

U.S. PATENT DOCUMENTS 5,976,546 A * 11/1999 Laus et al. ............. 424/192.1
6,080,409 A * 6/2000 Laus et al. ............. 424/192.1

FOREIGN PATENT DOCUMENTS

WO WO 2004/026238 A2 4/2004
WO WO 2004/031211 A2 4/2004

OTHER PUBLICATIONS

Seward et al. 'Peptides Presented by HLA-DR Molecules in Synovia of Patients with Rheumatoid Arthritis or Antibiotic-Refractory Lyme Arthritis.' Molecular & Cellular Proteomics. 10:10.1074/mcp.M110.002477, Jan.14, 2011. This paper is available on line at http://www.mcponline.org.*
Machlenkin, et al.; "Human CTL epitopes prostatic acid phosphatase-3 and six-transmembrane epithelial antigen of prostate-3 as candidates for prostate cancer immunotherapy"; *Cancer Research*; 65(14): 6435-6442 (Jul. 2005).
Matsueda, et al.; "Identification of peptide vaccine candidates for prostate cancer patients with HLA-A3 supertype alleles"; *Clinical Cancer Research*; 11(19): 6933-6943 (Oct. 2005).
Southwood, et al.; "Several common HLA-DR types share largely overlapping peptide binding repertoires"; *Journal of Immunology*; 160(7): 3363-3373 (Apr. 1998).
McNeel, D.G. et al., "Identification of T Helper Epitopes from Prostatic Acid Phospatase," Jul. 1, 2001, Cancer Research, vol. 61, pp. 5161-5167.

* cited by examiner

*Primary Examiner* — Nora Rooney
(74) *Attorney, Agent, or Firm* — Kilpatrick Townsend & Stockton LLP

(57) ABSTRACT

The present invention relates to the discovery of novel T cell epitopes of the human prostatic acid phosphatase (PAP) protein that is promiscuous for at least 15 different HLA-DR alleles. The invention also relates to compositions that contain one of the novel epitopes or a fusion peptide of such an epitope and a heterologous polypeptide. Further disclosed herein is the use of the epitopes or their fusion peptides, and compositions containing the epitopes or their fusion peptides.

18 Claims, 4 Drawing Sheets

PROMISCUOUS PAP CD4 T CELL EPITOPES

RELATED APPLICATIONS

This application claims priority to provisional U.S. Patent Application No. 60/837,053, filed Aug. 11, 2006, the contents of which are incorporated herein by reference in the entirety.

BACKGROUND OF THE INVENTION

HLA class II-restricted CD4+ T cells play a critical role in cellular immunity and are a key component of anti-tumor immune responses. CD4+ T cells provide necessary help to tumor-specific CTLs (Topalian 1994. *Curr Opin Immunol* 6:741-745) and produce cytokines such as interferon gamma (IFNγ), which can activate antigen presenting cells and mediate other immunological effects (Corthay et al., 2005. *Immunity* 22:371-383). Experimental results in several systems have demonstrated that CD4+ T cells are necessary for an effective anti-tumor immune response. Given the importance of CD4+ T cells in generating a robust immune response, an optimally designed cancer immunotherapy or anti-tumor vaccine should induce both tumor-specific CD4+ and CD8+ T cells for maximal efficacy.

The human prostatic acid phosphatase (PAP) is a phosphatase predominantly expressed in the prostate gland. Elevated serum level of PAP is often observed in patients with prostate cancer or other prostate conditions, with the highest levels of PAP found in metastasized prostate cancer. In addition, diseases of the bone, such as Paget's disease or hyperparathyroidism, diseases of blood cells, such as sickle-cell disease, multiple myeloma, or lysosomal storage diseases, such as Gaucher's disease, will show moderately increased levels of PAP. Because over 95% of prostate cancer cells express PAP, several immunotherapeutic strategies for prostate cancer have been devised using PAP as a target. For instance, *Cancer Biology and Therapy* (March 2005, vol. 4, issue 3) has reported promising results from a clinical study in which a patient's own immune cells were collected, stimulated to become immunoreactive to PAP, and then returned to the patient by intravenous injection. These new immunological approaches rely on methods that can effectively induce a PAP-specific immunity, including T cell-mediated immunity.

The usefulness of a defined T cell epitope is limited by its HLA-restriction. Peptide epitopes typically form productive peptide-MHC complexes with a small number of HLA alleles and stimulate T cell responses only in individuals expressing those alleles. This confines immunological studies and clinical trials to individuals of a specific HLA type, often 20% or less of the general population. So-called promiscuous T cell epitopes, which can be presented by a larger number of HLA alleles, have been described for several tumor antigens. Promiscuous T cell epitopes can bind to multiple HLA alleles to stimulate antigen-specific T cells, allowing for the induction and study of T cell responses in individuals of different HLA types. Additionally, promiscuous epitopes are valuable because the immunotherapies and vaccines based on these epitopes can be widely applicable to the general population for cancer treatment and prevention. Thus, there exists a clear need for new information relating to previously unknown promiscuous epitopes of tumor antigens, including PAP.

The present inventors have identified a series of novel promiscuous T cell epitopes in the human PAP protein sequence. These epitopes, comprising the region of 257-271 of the PAP protein, are recognized by a CD4+ T cell clone (PAPc66) in the context of HLA-DR and capable of inducing T cell activation when presented by antigen presenting cell of at least 15 different HLA-DRβ1* alleles. The promiscuity of these epitopes for different HLA-DRβ1* alleles makes these epitopes a valuable tool for evaluating PAP-specific immune responses regardless of the patient's HLA type. Additionally, these epitopes can be used as a universal CD4 T helper cell epitope in peptide-based vaccines or immunotherapies for the treatment PAP+ prostate cancers.

BRIEF SUMMARY OF THE INVENTION

The present invention describes novel PAP epitopes that can be presented by antigen presenting cells of a number of different HLA alleles to induce a PAP specific T cell response. In the first aspect, this invention provides an isolated peptide of 15-18 amino acids, which comprises a segment derived from the human PAP protein sequence (residues 257-271, i.e., SEQ ID NO:1). Preferably, the peptide consists of 15 to 18 contiguous amino acids of SEQ ID NO:2, which corresponds to the 254-274 segment of human PAP protein sequence. More preferably, the peptide has the sequence set forth in SEQ ID NO: 1. Also provided is a fusion product comprising the PAP derived peptide fused to a heterologous polypeptide. In some cases, the peptide is fused to the heterologous polypeptide by a peptide bond, such that the fusion product is in essence a recombinant fusion protein.

Preferably, the isolated peptide derived from the PAP sequence or its fusion product is capable of inducing a T cell immune response specific to a PAP protein when presented by an antigen-presenting cell of at least 10 different HLA-DR alleles, and more preferably, at least 11, 12, 13, 14, 15, or more different HLA-DR alleles.

In some embodiments, the HLA-DR alleles are selected from the group consisting of 0101, 0102, 0103, 1503, 160201, 0301, 0302, 0401, 0402, 040301, 040501, 1101, 1102, 1103, 1104, 110401, 1201, 1301, 1302, 1401, 1402, 0701, 080101, 080201, and 0901.

In some embodiments, the PAP derived peptide has the amino acid sequence of SEQ ID NO: 1. In other embodiments, the heterologous polypeptide is a granulocyte-macrophage colony-stimulating factor (GM-CSF).

In a second aspect, the present invention provides an isolated nucleic acid comprising a polynucleotide sequence encoding a PAP derived peptide described above or a fusion protein joining a PAP derived peptide and a heterologous polypeptide by a peptide bond, an expression cassette comprising the nucleic acid, and a host cell comprising the expression cassette.

In some cases, the polynucleotide sequence encodes the peptide having the amino acid sequence of SEQ ID NO: 1. In other cases, the polynucleotide sequence encodes a fusion protein in which the heterologous polypeptide is GM-CSF.

In some embodiments, the expression cassette is a recombinant viral vector. In other embodiments, the expression cassette directs the expression of the peptide having the amino acid sequence of SEQ ID NO: 1 or a recombinant fusion protein in which the heterologous polypeptide is GM-CSF.

In a third aspect, the present invention provides a composition comprising a PAP derived peptide as described above or a fusion product of the peptide fused with a heterologous polypeptide, in addition to a physiologically acceptable excipient.

In some embodiments, the peptide has the amino acid sequence of SEQ ID NO: 1. In other embodiments, the heterologous polypeptide is a granulocyte-macrophage colony-stimulating factor (GM-CSF). In yet other embodiments, the composition further comprises an antigen-presenting cell, which has the PAP derived peptide forming a complex with a major histocompatibility complex (MHC) molecule on the surface of the cell.

In a fourth aspect, the present invention provides a method for inducing in a patient a T cell immune response specific to a PAP protein. This method comprises the step of administering to the patient an effective amount of the composition comprising a PAP derived peptide as described above or a fusion product of the peptide fused with a heterologous polypeptide, as well as a physiologically acceptable excipient.

In some embodiments, the peptide has the amino acid sequence of SEQ ID NO: 1. In other embodiments, the heterologous polypeptide is a granulocyte-macrophage colony-stimulating factor (GM-CSF).

In a fifth aspect, the present invention provides a method for detecting in a patient a T cell immune response specific to a PAP protein. This method comprises the following steps: (a) obtaining an antigen-presenting cell and a T cell from the patient; (b) contacting the antigen-presenting cell and the T cell with a PAP derived peptide or a fusion product comprising the peptide and a heterologous polypeptide; and (c) detecting a T cell response, wherein the detection of a T cell response indicates the presence of a T cell immune response specific to a PAP protein in the patient.

In some embodiments, step (c) is performed by ELISPOT, proliferation assay, or flow cytometry. In other embodiments, the PAP derived peptide has the amino acid sequence of SEQ ID NO: 1.

BRIEF DESCRIPTION OF THE DRAWINGS

As shown in FIG. 2, the peptide can be presented in the context of HLA-DR or HLA-DQ. The assay was set up in 96 well round bottom plates with PAPc66 at $1 \times 10^5$ cells/well, $PAP_{257}$-271 at 2 µg/mL and $2 \times 10^5$ EBV-LcL per well in complete RPMI+10% FBS. Each HLA-DREBV-LcL line, homozygous for the HLA-DR131 allele shown, was tested for the ability to present $PAP_{257}$-271 to PAPc66. An irrelevant PAP peptide and no peptide control were also included. After 48-hour incubation at 37° C. and 5% $CO_2$, supernatants were tested for IFNγ and granzyme B (B) by ELISA. Results are shown with background (no peptide) for each EBV-LcL line and PAPc66 subtracted.

DEFINITIONS

Figure 1:
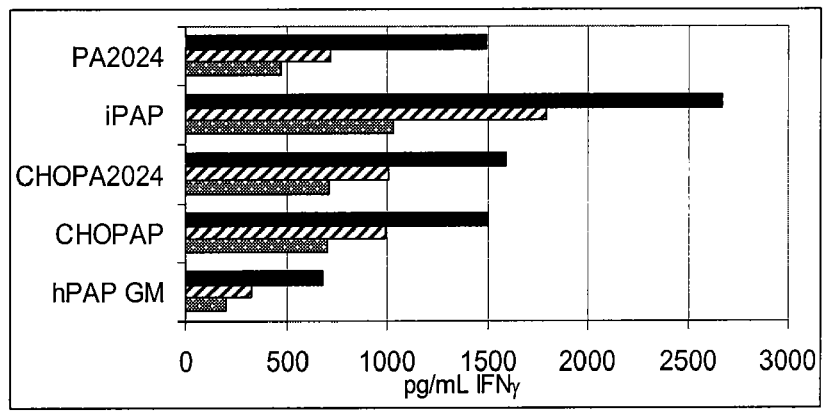
FIG. 1. T cell clone PAPc66 recognizes a naturally processed epitope from PAP. (A) PAP fusion proteins PA2024, CHOPA2024 and hPAPGM and PAP from a baculoviral expression system (iPAP) and mammalian expression system (CHOPAP) were titrated with autologous EBV-LcL and PAPc66. Assay was set up in 96 well round bottom plates with $1 \times 10^5$ cells/well of PAPc66, $2 \times 10^5$ cells/well EBV-LcL and antigens at 50 µg/mL (black bars), 25 µg/mL (stripe bars) and 12.5 µg/mL (dot bars) in complete RPMI media with 10% FBS. Assay was incubated for 48 hours at 37° C. with 5% $CO_2$ at which time supernatants were harvested and tested for IFNγ by ELISA. (B) To map the specific PAP peptide, chemically synthesized peptides from the PAP sequence were used. These 94 peptides were 15 amino acids in length overlapping by 11 amino acids and were individually tested for the ability to stimulate PAPc66 using autologous EBV-LcL and each peptide at 2 µg/mL in the assay. The assay was set up as in (A) and supernatants were tested for IFNγ by ELISA. (C) Peptide #65, $PAP_{257-271}$, was titrated with autologous EBV-LcL and PAPc66 in an assay set up as in (A). Supernatants were analyzed for peptide specific IFNγ production by ELISA.
Figure 1:
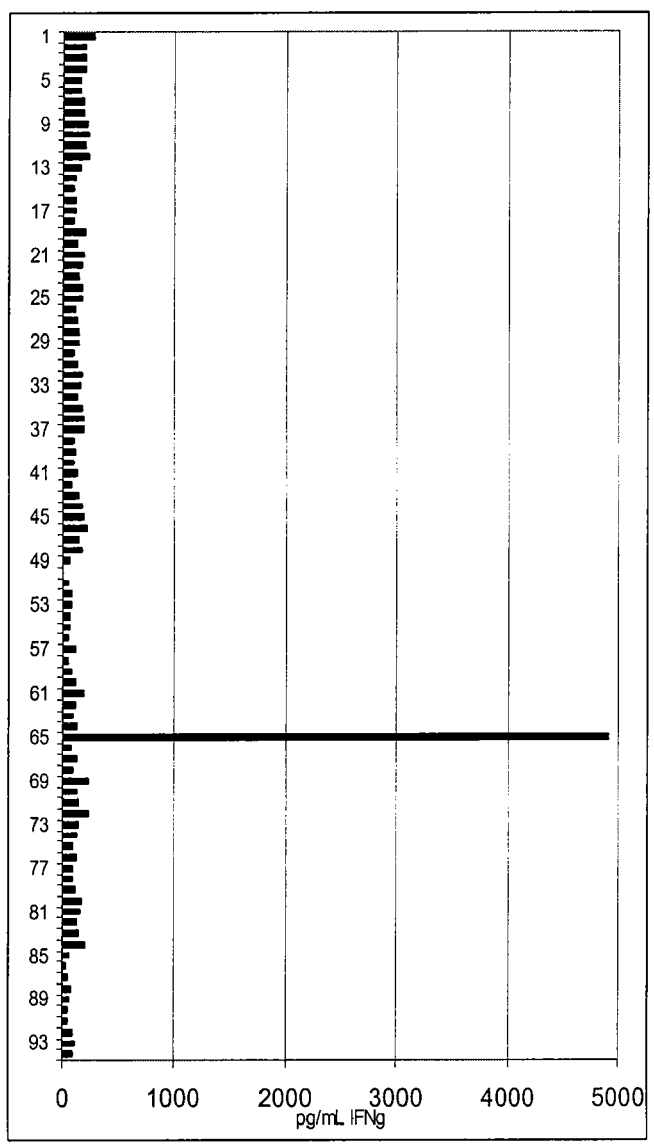
Figure 1:
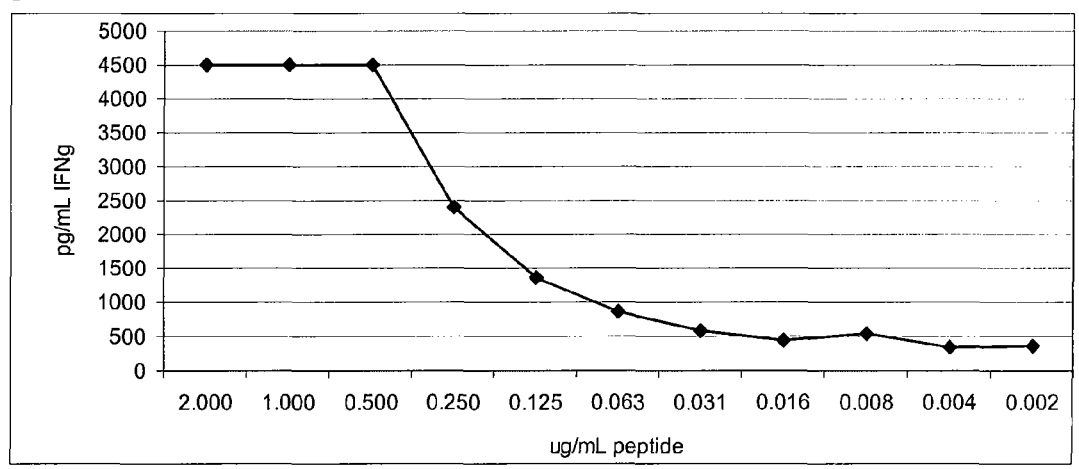

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

In this application, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure different from the general chemical structure of an amino acid, but capable of functioning in a manner similar to a naturally occurring amino acid.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, or mRNA encoded by a gene.

When the relative locations of elements in a polynucleotide sequence are concerned, a "downstream" location is one at the 3' side of a reference point, and an "upstream" location is one at the 5' side of a reference point.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds. In this application, the amino acid sequence of a polypeptide is presented from the N-terminus to the C-terminus. In other words, when describing an amino acid sequence of a peptide, the first amino acid from the N-terminus is referred to as the "first amino acid."

When used in the context of describing partners of a fusion peptide, the term "heterologous" refers to the relationship of one peptide fusion partner to the another peptide fusion partner: the manner in which the fusion partners are present in the fusion peptide is not one that can be found a naturally occurring protein. For instance, a "heterologous polypeptide" fused with a promiscuous prostatic acid phosphatase (PAP) epitope to form a fusion peptide may be one that is originated from a protein other than the PAP protein, such as a granulocyte-macrophage colony-stimulating factor (GM-CSF). On the other hand, a "heterologous polypeptide" may be one derived from another portion of the PAP protein that is not immediately contiguous to the promiscuous epitope. A "heterologous polypeptide" may contain modifications of a naturally occurring protein sequence or a portion thereof, such as deletions, additions, or substitutions of one or more amino acid residues. Regardless of the origin of the "heterologous polypeptide" (i.e., whether it is derived from the PAP protein or another protein), the fusion peptide should not contain a subsequence of the PAP protein that encompasses the amino acid sequence of SEQ ID NO: 1 and have more than 18 amino acids in length. In some exemplary embodiments, a "heterologous polypeptide" for use in the present invention has no more than 15-20 amino acids in length; in other embodiments, a "heterologous polypeptide" has at least 100 amino acids in length.

The word "fuse" or "fused," as used in the context of describing a peptide of this invention that comprises a promiscuous PAP epitope joined with a heterologous polypeptide, refers to a connection between the epitope and the heterologous polypeptide by any covalent bond, including a peptide bond.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform to codon preference in a specific host cell.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

The term "recombinant," when used with reference, e.g., to a cell, or nucleic acid, protein, or vector, indicates that the cell, nucleic acid, protein or vector, has been modified by the introduction of a nucleic acid or protein from an outside source or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all.

The term "administration" or "administering" refers to various methods of contacting a substance with a mammal, especially a human. Modes of administration may include, but are not limited to, methods that involve contacting the substance intravenously, intraperitoneally, intranasally, transdermally, topically, subcutaneously, parentally, intramuscularly, orally, or systemically, and via injection, ingestion, inhalation, implantation, or adsorption by any other means. One exemplary means of administration of the promiscuous PAP peptide of this invention or a fusion peptide comprising the PAP peptide and a heterologous polypeptide is via intravenous delivery, where the peptide or fusion peptide can be formulated as a pharmaceutical composition in the form suitable for intravenous injection, such as an aqueous solution, a suspension, or an emulsion, etc. Other means for delivering the promiscuous PAP peptide or a fusion peptide of this invention includes intradermal injection, subcutaneous injection, intramuscular injection or transdermal application as with a patch.

An "effective amount" of a certain substance refers to an amount of the substance that is sufficient to effectuate a desired result. For instance, an effective amount of a composition comprising a peptide of this invention that is intended to induce an anti-PAP immunity is an amount sufficient to achieve the goal of inducing the immunity when administered to a subject. The effect to be achieved may include the prevention, correction, or inhibition of progression of the symptoms of a disease/condition and related complications to any detectable extent. The exact quantity of an "effective amount" will depend on the purpose of the administration, and can be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

A "physiologically acceptable excipient" is an inert ingredient used in the formulation of a composition of this invention, which contains the active ingredient(s) of a promiscuous PAP peptide or a fusion peptide comprising the PAP peptide and a heterologous polypeptide and is suitable for use, e.g., by injection into a patient in need thereof. This inert ingredient may be a substance that, when included in a composition of this invention, provides a desired pH, consistency, color, smell, or flavor of the composition.

As used herein, the term "T cell immune response" refers to activation of antigen specific T cells as measured by proliferation or expression of molecules on the cell surface or secretion of proteins such as cytokines.

DETAILED DESCRIPTION OF THE INVENTION

I. Introduction

The present inventors have identified novel promiscuous T cell epitopes from the human prostatic acid phosphatase (PAP) protein. These peptide epitopes demonstrate remarkable HLA promiscuity as they can be presented in the context of at least 9 different HLA-DR serological families and at least 15 different HLA-DRβ1 alleles. The presentation of these epitopes by such a wide range of HLA-DRβ1 alleles makes the epitopes extremely valuable as universal CD4 T helper cell epitopes in preparation of vaccines or immunotherapies for the treatment of prostate cancer overexpressing the PAP protein in the general human population.

II. Chemical Synthesis of Peptides

The peptides of the present invention, particular those of relatively short length (e.g., no more than 50-100 amino acids), may be synthesized chemically using conventional peptide synthesis or other protocols well known in the art.

Peptides may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, e.g., Atherton et al., *Solid Phase Peptide Synthesis: A Practical Approach*, IRL Press (1989), and Bodanszky, *Peptide Chemistry, A Practical Textbook,* 2nd Ed., Springer-Verlag (1993)).

III. Recombinant Production of Peptides

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange HPLC as described in Pearson & Reanier, *J. Chrom.* 255:137-149 (1983).

Recombinant production is an effective means to obtain peptides of this invention, particularly those of relatively large molecular weight, for example, a fusion peptide of a promiscuous PAP epitope and a GM-CSF. The sequence of a polynucleotide encoding a peptide of this invention, and synthetic oligonucleotides can be verified after cloning or subcloning using, e.g., the chain termination method for sequencing double-stranded templates of Wallace et al., *Gene* 16: 21-26 (1981).

B. Construction of an Expression Cassette

Obtaining a Polynucleotide Sequence Encoding a Peptide of the Invention

A polynucleotide sequence encoding a peptide of this invention can be obtained by chemical synthesis, or can be purchased from a commercial supplier, which may then be further manipulated using standard techniques of molecular cloning.

Modification of Nucleic Acids for Preferred Codon Usage in a Host Organism

The polynucleotide sequence encoding a peptide of this invention can be optionally altered to coincide with the preferred codon usage of a particular host. For example, the preferred codon usage of one strain of bacterial cells can be used to derive a polynucleotide that encodes a peptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the peptides of this invention.

Following verification of the coding sequence, the peptide of the present invention can be produced using routine techniques in the field of recombinant genetics.

C. Expression Systems

To obtain high level expression of a nucleic acid encoding a peptide of the present invention, one typically subclones a polynucleotide encoding the peptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing a peptide of this invention are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of a peptide of this invention in host cells. A typical expression cassette thus contains a promoter operably linked to the polynucleotide sequence encoding the peptide and signals required for efficient polyadenylation of the transcript, ribosome binding sites, and translation termination. The nucleic acid sequence encoding the peptide is typically linked to a cleavable signal peptide sequence to promote secretion of the peptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene (e.g., encoding the heterologous polypeptide), introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the peptide of this invention under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., a peptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

C. Transfection Methods

Standard transfection methods are used to produce bacterial, mammalian, yeast, insect, or plant cell lines that express large quantities of a peptide of this invention, which are then purified using standard techniques (see, e.g., Colley et al., *J. Biol. Chem.* 264:17619-17622 (1989); *Guide to Protein Purification,* in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the peptide of this invention.

D. Detection of Recombinant Expression of a Peptide in Host Cells

After the expression vector is introduced into appropriate host cells, the transfected cells are cultured under conditions favoring expression of the peptide of this invention. The cells are then screened for the expression of the recombinant peptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a peptide of this invention in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a peptide of the present invention, particularly one containing a sufficiently large heterolougs polypeptide (e.g., Harlow and Lane, *Antibodies, A Laboratory Manual*, Chapter 14, Cold Spring Harbor, 1988; Kohler and Milstein, *Nature*, 256: 495-497 (1975)). Such techniques require antibody preparation by selecting antibodies with high specificity against the peptide or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.*, 6: 511-519 (1976).

IV. Purification of Peptides

A. Purification of Chemically Synthesized Peptides

Purification of synthetic peptides is accomplished using various methods of chromatography, such as reverse phase HPLC, gel permeation, ion exchange, size exclusion, affinity, partition, or countercurrent distribution. The choices of appropriate matrices and buffers are well known in the art.

B. Purification of Recombinantly Produced Peptides

1. Purification of Peptides from Bacterial Inclusion Bodies

When a peptide of the present invention is produced recombinantly by transformed bacteria in large amounts, typically after promoter induction, although expression can be constitutive, the peptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18:182-190 (2000).

Alternatively, it is possible to purify recombinant polypeptides, e.g., a peptide of this invention, from bacterial periplasm. Where the recombinant polypeptide is exported into the periplasm of the bacteria, the periplasmic fraction of the bacteria can be isolated by cold osmotic shock in addition to other methods known to those of skill in the art (see e.g., Ausubel et al., supra). To isolate recombinant peptides from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant peptides present in the supernatant can be separated from the host proteins by standard separation techniques well known to those of skill in the art.

2. Standard Protein Separation Techniques for Purification

When a recombinant polypeptide, e.g., a peptide of the present invention, is expressed in host cells in a soluble form, its purification can follow the standard protein purification procedure described below. This standard purification procedure is also suitable for purifying peptides obtained from chemical synthesis.

i. Solubility Fractionation

Often as an initial step, and if the protein mixture is complex, an initial salt fractionation can separate many of the unwanted host cell proteins (or proteins derived from the cell culture media) from the recombinant protein of interest, e.g., a peptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a peptide of the present invention. The retentate of the ultrafiltration is then ultrafiltered against a membrane with a molecular cut off greater than the molecular weight of the peptide of interest. The recombinant protein will pass through the membrane into the filtrate. The filtrate can then be chromatographed as described below.

iii. Column Chromatography

A protein of interest (such as a peptide of the present invention) can also be separated from other proteins on the basis of its size, net surface charge, hydrophobicity, or affinity for ligands. In addition, antibodies raised against a peptide of this invention can be conjugated to column matrices and the peptide immunopurified. All of these methods are well known in the art.

It will be apparent to one of skill that chromatographic techniques can be performed at any scale and using equipment from many different manufacturers (e.g., Pharmacia Biotech).

C. Confirmation of Peptide Sequence

The amino acid sequence of a peptide of this invention can be confirmed by a number of well established methods. For example, the conventional method of Edman degradation can be used to determine the amino acid sequence of a peptide. Several variations of sequencing methods based on Edman degradation, including microsequencing, and methods based on mass spectrometry are also frequently used for this purpose.

D. Modification of Peptides

The peptides of the present invention can be modified to achieve more desirable properties. The design of chemically modified peptides and peptide mimics that are resistant to degradation by proteolytic enzymes or have improved solubility or binding ability is well known.

Modified amino acids or chemical derivatives of a promiscuous PAP peptide or fusion peptides of this invention may contain additional chemical moieties of modified amino acids not normally a part of the PAP protein. Covalent modifications of the peptides are within the scope of the present invention. Such modifications may be introduced into a peptide by reacting targeted amino acid residues of the peptide with an organic derivatizing agent that is capable of reacting with selected side chains or terminal residues. The following examples of chemical derivatives are provided by way of illustration and not by way of limitation.

The design of peptide mimics which are resistant to degradation by proteolytic enzymes is known to those skilled in the art. See e.g., Sawyer, *Structure-Based Drug Design*, P. Verapandia, Ed., N.Y. (1997); U.S. Pat. Nos. 5,552,534 and 5,550,251. Both peptide backbone and side chain modifications may be used in designing secondary structure mimicry. Possible modifications include substitution of D-amino acids, $N^\alpha$-Me-amino acids, $C_\alpha$-Me-amino acids, and dehydroamino acids. To this date, a variety of secondary structure mimetics have been designed and incorporated in peptides or peptidomimetics.

Other modifications include substitution of a natural amino acid with an unnatural hydroxylated amino acid, substitution of the carboxy groups in acidic amino acids with nitrile derivatives, substitution of the hydroxyl groups in basic amino acids with alkyl groups, or substitution of methionine with methionine sulfoxide. In addition, an amino acid of a promiscuous PAP peptide or a fusion peptide of this invention can be replaced by the same amino acid but of the opposite chirality, i.e., a naturally-occurring L-amino acid may be replaced by its D-configuration.

V. Fusing a PAP Epitope with a Heterologous Polypeptide

In one aspect of this invention, a peptide corresponding to a promiscuous PAP epitope is attached to a heterologous polypeptide via a covalent bond to form a fusion peptide, such that the ability of the PAP epitope to induce a T cell response is enhanced. Frequently, this covalent bond is a peptide bond and the PAP epitope and the heterologous polypeptide form a new polypeptide. This peptide bond may be a direct peptide bond between the PAP epitope and the heterologous polypeptide, or it may be an indirect peptide bond provided by way of a peptide linker between the PAP epitope and the heterologous polypeptide.

Other covalent bonds are also suitable for the purpose of fusing the PAP peptide with the heterologous polypeptide. For instance, a functional group (such as a non-terminal amine group, a non-terminal carboxylic acid group, a hydroxyl group, and a sulfhydryl group) of one peptide may easily react with a functional group of the other peptide and establish a covalent bond, other than a peptide bond, that conjugates the two peptides. A covalent connection between a peptide of a promiscuous PAP epitope and a heterologous polypeptide can also be provided by way of a linker molecule with suitable functional group(s). Such a linker molecule can be a peptide linker or a non-peptide linker. A linker may be derivatized to expose or to attach additional reactive functional groups prior to conjugation. The derivatization may involve attachment of any of a number of molecules such as those available from Pierce Chemical Company, Rockford, Ill.

VI. Functional Assays

A promiscuous PAP epitope of this invention (or a fusion peptide comprising the PAP peptide and a heterologous polypeptide) is useful for its capability to induce a T cell immune response specific to a PAP protein, when the epitope is presented by an antigen-presenting cell that may have one of at least 10 different HLA-DR alleles, more preferably at least 12, 13, 14, or 15 different HLA-DR alleles. Various functional assays can be used to confirm the ability of a promiscuous PAP epitope to induce such a PAP-specific T cell immune response in a promiscuous manner with regard to antigen presenting cells of different HLA-DR alleles, including proliferation assay and flow cytometry assays detecting the binding between a T cell receptor and a peptide epitope or the production of cytokines by T cells.

The functional assay system used in the Examples of this application is particularly suitable for this purpose. Briefly, a panel of at least 10, preferably at least 12, 13, 14, 15 or more antigen presenting cell lines, each homozygous for a different HLA-DR allele, is employed to present a PAP-derived peptide to a CD4+ T cell clone (e.g., clone PAPc66) that is specifically responsive to the PAP protein (e.g., by production of cytokines such as IFNγ or granzyme B). The peptide corresponding to residues 257-271 of the human PAP protein (i.e., SEQ ID NO: 1) is used as a positive control. An irrelevant PAP-derived peptide, no peptide, and each antigen presenting cell line alone are used as negative controls for the assays. The assays are set up in multi-welled cell culture plates in appropriate medium with antigen presenting cells and CD4+ T cells in each well. Peptides are diluted to a suitable concentration and added to each well. Following incubation of an appropriate time period, supernatants are collected from the wells and analyzed for cytokine production, which can be measured by ELISA based on absorbance at 492 nm. Typically, the effect of a PAP class II promiscuous epitope of this invention in inducing a PAP-specific CD4+ T cell response is at least 25% of the effect of PAP epitope 257-271 (which has the amino acid sequence set forth in SEQ ID NO: 1) under the same assay conditions, e.g., at the same molar concentration and presented by antigen-presenting cells of the same, individual HLA-DR allele. More preferably such effect is at least 30%, 40%, 50%, 60%, 70%, 80% or higher of that shown by PAP epitope 257-271 under the same conditions.

VII. Compositions and Administration

The present invention also provides compositions comprising an effective amount of (1) a promiscuous PAP peptide; or (2) a fusion peptide comprising a PAP peptide and a heterologous polypeptide; or (3) an antigen presenting cell (APC) with the peptide of (1) or (2) forming a complex with an MHC molecule on the cell surface for inducing a T cell immune response specific against a PAP protein in both prophylactic and therapeutic applications. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

Antigen presenting cells (APCs) can be generated for peptide loading by a variety of methods. The starting raw material is peripheral blood or a leukapheresis with or without mobilization. APCs can be isolated by multiple methods, e.g., buoyant density centrifugation, elutriation, magnetic beads and plastic adherence used alone or in combination. After isolation, APCs are cultured for 1-14 days with or without the presence of cytokines, growth factors, activation agents and maturation agents. APCs are loaded with peptide by addition of peptide to the culture in concentrations from 1 µg to 1 mg/mL for 6-48 hrs. APCs are then harvested, washed and resuspended in a suitable formulation for infusion. APCs can be delivered fresh or can be kept in frozen storage for delivery at a later time.

The pharmaceutical compositions of the present invention can be administered by various routes, e.g., subcutaneous, intradermal, transdermal, intramuscular, intravenous, or intraperitoneal. The preferred routes of administering the pharmaceutical compositions are subcutaneous or intradermal at biweekly doses of about 1 µg-10 mg, preferably 50 µg-1 mg, of a peptide of this invention for a 70 kg adult human. The appropriate dose may be administered in weekly, biweekly, or monthly intervals.

Peptide pulsed APCs can be administered by various routes, e.g., subcutaneous, intradermal, intravenous or intraperitoneal. The peptide pulsed APCs are delivered in weekly, biweekly, or monthly intervals at doses of 1 million to 10 billion cells.

For preparing pharmaceutical compositions containing a peptide of the present invention, inert and pharmaceutically acceptable excipients or carriers are used. Liquid pharmaceutical compositions include, for example, solutions, suspensions, and emulsions suitable for intradermal, subcutaneous, parenteral, or intravenous administration. Sterile water solutions of the active component (e.g., a promiscuous PAP peptide or fusion peptide) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a promiscuous PAP peptide or fusion peptide) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing a PAP peptide or fusion peptide can be administered for prophylactic and/or therapeutic treatments. In therapeutic applications, compositions are administered to a patient already suffering from a condition that may be exacerbated by the proliferation of tumor cells overexpression the PAP protein in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 1 µg to about 10 mg of the PAP peptide or fusion peptide biweekly for a 70 kg patient, with dosages of from about 50 µg to about 1 mg of the peptide biweekly for a 70 kg patient being more commonly used. The appropriate dose may be administered in weekly, biweekly, or monthly intervals.

Single or multiple administrations of the compositions can be carried out with dose levels and pattern being selected by the treating physician. In any event, the pharmaceutical formulations should provide a quantity of a PAP peptide or fusion peptide of this invention sufficient to effectively inhibit PAP-expressing tumor cell proliferation in the patient for therapeutic purposes.

VIII. Method for Detecting T Cell Response Specific to PAP

The present invention further provides a method for detecting whether a T cell immune response specific to a PAP protein is present in a patient. This method includes the following steps: first, lymphocytes including at least a T cell and an antigen-presenting cell are obtained from a patient. Suitable samples that yield such lymphocytes include blood, tumor infiltrate, and lymph nodes or lymphatic fluids. Second, the T cell and antigen-presenting cells are exposed to a promiscuous PAP peptide (or a fusion peptide comprising the PAP peptide and a heterologous peptide) of this invention under conditions that would allow proper presentation of a T cell epitope by the antigen-presenting cell to the T cell. Third, signs of a T cell response is measured in vitro by means well known in the art such as ELISPOT, proliferation assay, or flow cytometry. When a T cell response is detected by any of these methods, it can be concluded that there exists a T cell immune response specific to a PAP protein in the patient.

EXAMPLES

The following examples are provided by way of illustration only and not by way of limitation. Those of skill in the art will readily recognize a variety of non-critical parameters that could be changed or modified to yield essentially similar results.

Example 1

Materials and Methods

Recombinant Proteins and Synthetic Peptides. PA2024 is a proprietary recombinant fusion protein containing PAP and GM-CSF sequences manufactured by Dendreon Corporation for the investigational cellular immunotherapy sipuleucel-T. PA2024 is expressed in a baculovirus system. CHOPA2024 and hPAPGM are sequence identical to PA2024 but expressed in mammalian systems using Chinese Hampster Ovary cells (CHO) and 293 Ebna respectively. iPAP is a recombinant protein produced in a baculovirus expression system and CHOPAP is a recombinant protein produced in mammalian cells, both produced and purified by Dendreon Corporation. For defining PAP specific immune responses in vitro, 94 peptides were generated from the PAP protein sequence. These peptides were 15 amino acids in length, overlapping by 11 amino acids (Genemed Synthesis, South San Francisco, Calif.). All PAP peptides were sequenced and determined to be >95% pure by analytical HPLC and mass spectroscopy.

Subject and Healthy Donor Sample Collection. All subject and healthy donor specimens were collected according to investigator-sponsored protocols approved by the appropriate Investigational Review Board. Following informed consent, whole blood samples were collected by venipuncture into heparinized vacutainer tubes or syringes and prepared for transport and/or processing. After receipt of blood samples by the laboratory, peripheral blood mononuclear cells (PBMC) were collected under sterile conditions by density gradient centrifugation and prepared for use in specified assays.

Cell Lines. HLA-DRβ1 EBV-LcL lines were purchased from the European Collection of Cell Cultures originating from the 12$^{th}$ International Histocompatibility Workshop (IHW) held in Strasbourg, France. HLA-DR EBV-transformed lymphoblastoid cells were homozygous for the HLA-DRβ1 allele (Table I). EBV-LcL were also generated from various subject PBMC using supernatant from the B95-8 cell line (ATCC, Manassas, Va.) for the expansion and testing of autologous T cell clones.

In Vitro Generation of PAP specific T cell clones. PBMC from a subject receiving sipuleucel-T were stimulated in a T-25 tissue culture flask with 10 µg/mL of CHOPA2024 overnight in RPMI 1640 with 2 mM L-glutamine, 50 U/mL Penicillin, 50/g/mL Streptomycin and 20 mM HEPES buffer with 10% Human AB serum (Gemini BioProducts, Calabasas, Calif.) (cRPMI+10% HS). The following day, IFNγ secreting cells were isolated from the PBMC culture using the IFNγ Secretion Assay Cell Enrichment and Detection kit (Miltenyi Biotech, Auburn, Calif.). The IFNγ enriched population was plated for cloning in 96 well round bottom plates at approximately 1-50 cells/well with 10 U/mL recombinant human IL-2 (Invitrogen). Non-IFNγ secreting cells were irradiated (3000 rads) and used as feeder cells. Plates were incubated for seven days at 37° C. with 5% $CO_2$. On day 7 of the cloning, IFNγ secreting cells were non-specifically expanded in 96 well plates as previously described (Yee et al., *Proc. Natl. Acad. Sci*, 99: 16168-16173). Briefly, 100 µL of cRPMI+10% HS media with 25 U/mL recombinant human IL-2 and 10 ng/mL anti-human CD3 antibody (BD Pharmingen, San Diego, Calif.) was added to each well with $1 \times 10^4$/well irradiated autologous EBV-LcLs and $1 \times 10^5$/well irradiated allogeneic PBMC. Plates were incubated for 14 days at 37° C. with 5% $CO_2$ and then visually inspected for positive growth. Growth positive clones were transferred into 24 well plates and expanded using rIL-2, anti-CD3 and accessory cells as above, adjusting cell numbers for the increased volume.

Antigen Specificity of T cell clones. All assays were set up in triplicate in 96-well round bottom plates with antigen or peptide in cRPMI 1640+10% FBS (Fetal Bovine Serum (Invitrogen, Carlsbad, Calif.)), T cell clones at $1 \times 10^5$ cells/well and antigen presenting cells at $2 \times 10^5$ cells/well. Autologous EBV-LcL were used for antigen presenting cells in specificity assays and assays conducted to show peptide promiscuity using the HLA-DRB1 EBV-LcLs. All assays were incubated for 48 hours at 37° C. with 5% $CO_2$. After 48 hours, supernatants were harvested to assay for cytokine production. MHC Class II blocking assays were set up as above with autologous EBV-LcL and the addition of the following antibodies (25 µg/mL-0.1 µg/mL) to the assay: anti-HLA-DR mAb (Dendreon Corporation and Research Diagnostics, Inc. Flanders, N.J.), HLA-DQ mAb 1a3 and HLA-DP mAb B7/21 (Leinco Technologies, St. Louis, Miss.). Anti-HLA-A2 mAb (HB-82, ATCC, Manassas, Va.) was used as a control in blocking assays.

IFNγ and Granzyme B ELISA. IFN□ production was measured using anti-human IFNγ antibody pairs for ELISA (BD Pharmingen, San Diego, Calif.). Briefly, Immulon 4 plates (Thermo Labsystems/VWR, Brisbane, Calif.) were coated overnight with 100 µL of anti-human IFNγ antibody at 3 µg/mL. Plates were blocked with 4% Bovine Serum Albumin (BSA) (Sigma, St. Louis, Mo.) in PBS (Invitrogen) for 2 hours at 37° C. Plates were washed with PBS+0.05% Tween 20 and 100 µL of supernatant samples from the antigen specific stimulation was added to wells and incubated at room temperature for 1.25-2 hours. Plates were washed and biotinylated anti-human IFNγ antibody was diluted in 1% BSA in PBS (1 µg/mL) and added to plates in 100 µL for 1 hour at room temperature. After washing, Strep-Avidin HRP (BD Pharmingen) was diluted 1:1000 in PBST and added to wells for 30 minutes at room temperature. Plates were washed incubated with Sigma Fast OPD for 15 minutes in the dark. 2M HCl was added to stop the reaction and plates were read for absorbance at 492 nm on a spectrophotometer. Granzyme B ELISA kit (Cat. No. 3485-1H-20, Mabtech, Nacka Strand, Sweden) was used to measure granzyme B production. Coating antibody (GB10), biotinylated detection antibody (GB11) and Strep-Avidin-BRP were used according to manufacturer's recommendations under the protocol described above.

Results

Figure 2:
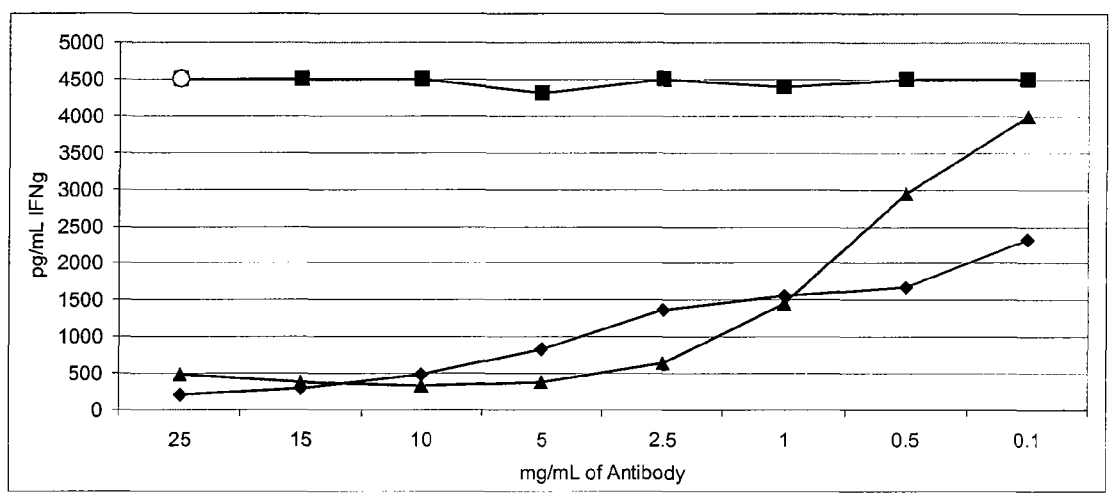
FIG. 2. $PAPc66_1$ is MHC class II restricted. PAPc66 was stimulated with autologous EBV-LcL at $2 \times 10^5$ cells/mL and $PAP_{257-271}$ at 2 µg/mL in the presence of MHC Class II blocking antibodies. The assay was set up in 96 well round bottom plates in complete RPMI media+10% FBS with anti-HLA-DR ♦ (Dendreon) and anti-HLA-DP ■ or anti HLA-DQ ▲ (Leinco Technologies, Inc., St. Louis, Mich.) at the concentrations shown. Anti-HLA-A2 antibody (○) was used as a negative control. PAPc66 was added to all wells at $1 \times 10^5$ cells/well and the assay was incubated for 48 hours at 37° C. and 5% $CO_2$. After the incubation, supernatants were harvested and tested for IFNγ by ELISA. IFNγ was not detected for conditions without peptide. These results indicate that $PAP_{257-271}$ is presented both in the context of HLA-DR and HLA-DQ.
Figure 3:
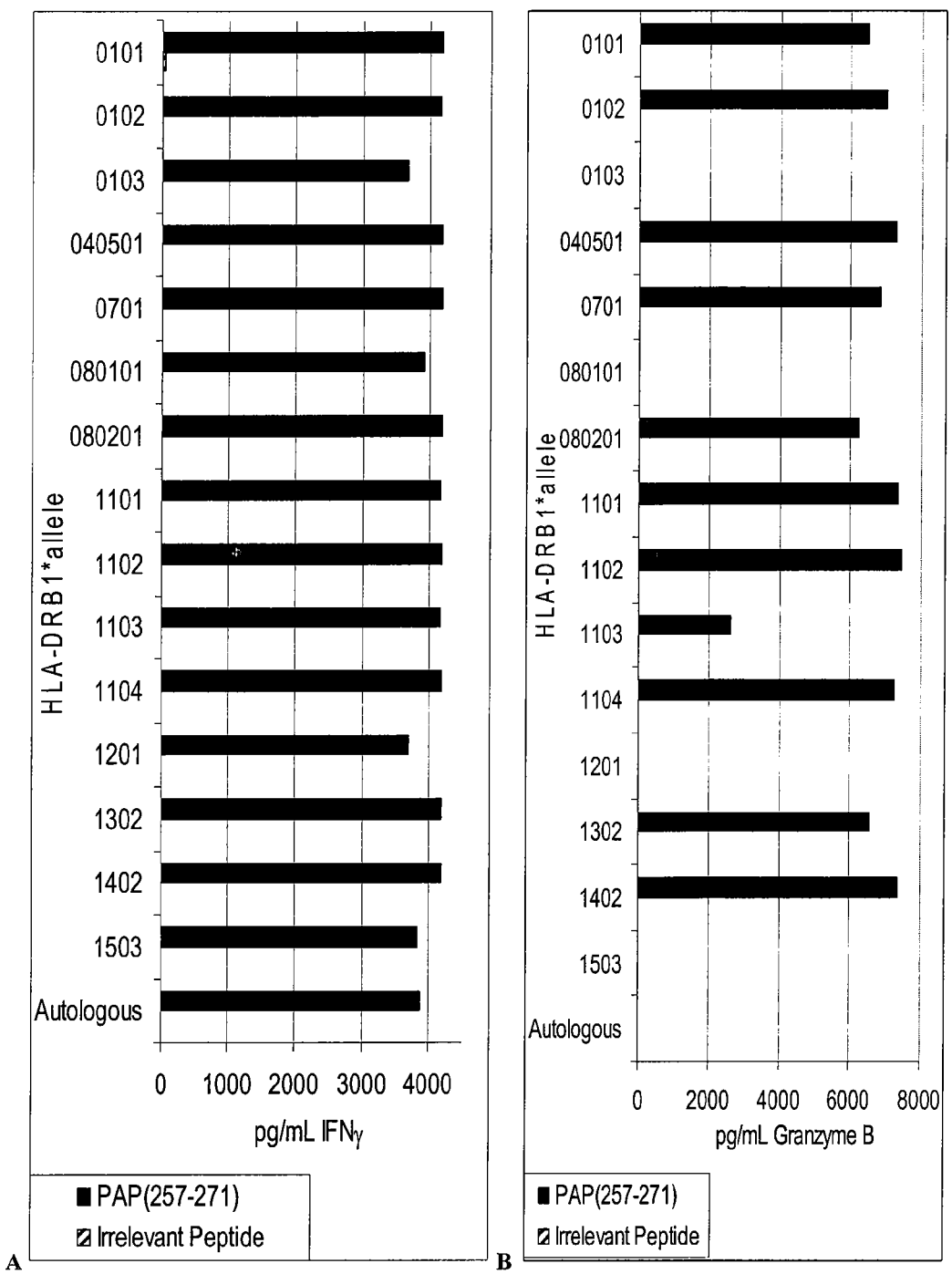
FIG. 3. $PAP_{257-271}$ is a promiscuous MHC class II PAP epitope recognized by the T cell clone PAPc66. (A) The peptide, $PAP_{257-271}$(RLQGGVLVNEILNHM; SEQ ID NO:1), recognized by a CD4+ T-cell clone (PAPc66) in the context of MHC class II, is capable of inducing T-cell activation when presented by lymphoblastoid cell lines representing 9 different HLA-DR serological families (β chain; DR1, DR4, DR7, DRB, DR11, DR12, DR13, DR14, DR15) having over 15 distinct HLA-DRβ1 alleles.

The experimental results shown in FIGS. 1-3 demonstrate that peptide $PAP_{257-271}$ is a naturally processed, MHC class II-restricted promiscuous epitope of prostatic acid phosphatase (PAP). This peptide has the amino acid sequence as shown in SEQ ID NO: 1 (RLQGGVLVNEILNHM), is capable of inducing T-cell activation when presented by lymphoblastoid cell lines representing 9 different HLA-DR serological families (β chain; DR1, DR4, DR7, DR8, DR11, DR12, DR13, DR14, and DR15) having over 15 different HLA-DRβ1 alleles.

The CD4+ T cell clone, PAPc66, was isolated from a subject participating in an ongoing phase 3 clinical trial for the treatment of prostate cancer using sipuleucel-T, which is an investigational autologous active cellular immunotherapy product designed to stimulate T-cell immune responses against human PAP. After an overnight stimulation of subject peripheral blood mononuclear cells with a fusion protein of PAP and human granulocyte-macrophage colony-stimulating factor (PA2024), PAPc66 was isolated using IFNγ secretion as a marker for selection. The clinical trial subject from whom this clone was isolated was typed as HLA-DRB1*0404, 1501. This clone has also been shown to produce IFNγ and granzyme B upon activation with appropriately presented $PAP_{257-271}$.

This novel promiscuous epitope provides a tool for investigating the potential immune mechanisms occurring as a consequence of treatment with PAP-specific, active cellular immunotherapy. Additionally, this peptide contributes to more universal targeting strategies for enhancing future cancer immunotherapies.

TABLE I

HLA-defined EBV-LCL cell lines.

| HLA-DRB1* allele | DR serological family | Cell line name |
|---|---|---|
| 0101 | DR1 | KAS116 |
| 0102 | DR1 | PMG075 |
| 0103 | DR103 | TER-ND |
| 1503 | DR15 | AMAI |
| 160201 | DR16 | RML |
| 0301 | DR17 | VAVY |
| 0302 | DR18 | RSH |
| 0401 | DR4 | BM14 |
| 0402 | DR4 | YAR |
| 040301 | DR4 | SSTO |
| 040501 | DR4 | LKT3 |
| 1101 | DR11 | BM21 |
| 1102 | DR11 | BM15 |
| 1103 | DR11 | TISI |
| 1104 | DR11 | BOB |
| 110401 | DR11 | FPAF |
| 1201 | DR12 | BM16 |
| 1301 | DR13 | OMW |
| 1302 | DR13 | EMJ |
| 1401 | DR14 | EK |
| 1402 | DR14 | AMALA |
| 0701 | DR7 | BER |
| 080101 | DR8 | BM9 |
| 080201 | DR8 | SPL |
| 0901 | DR9 | T7526 |

Cell lines were obtained from the ECACC European Collection of Cell Cultures and are listed in the IMGT/HLA cell directory (website ebi.ac.uk/imgt/hla/cell query.html).

All patents, patent applications, and other publications cited in this application, including published amino acid or polynucleotide sequences, are incorporated by reference in the entirety for all purposes.

What is claimed is:

1. An isolated peptide consisting of 15 to 18 amino acids and comprising the amino acid sequence of SEQ ID NO:1.

2. A fusion peptide consisting of the isolated peptide of claim 1 fused to a heterologous peptide.

3. The fusion peptide of claim 2, wherein the isolated peptide of claim 1 is fused to the heterologous peptide via a peptide bond.

4. The isolated peptide of claim 1, which induces a T cell immune response specific to human prostatic acid phosphatase (PAP) protein when presented by an antigen-presenting cell in the context of at least 10 different HLA-DR alleles.

5. The isolated peptide of claim 4, which induces a T cell immune response specific to a PAP protein when presented by an antigen-presenting cell in the context of at least 15 different HLA-DR alleles.

6. The isolated peptide of claim 4, wherein the HLA-DR alleles are selected from the group consisting of 0101, 0102, 0103, 1503, 160201, 0301, 0302, 0401, 0402, 040301, 040501, 1101, 1102, 1103, 1104, 110401, 1201, 1301, 1302, 1401, 1402, 0701, 080101, 080201, and 0901.

7. The isolated peptide of claim 1, which consists of the amino acid sequence of SEQ ID NO:1.

8. The fusion peptide of claim 2, wherein the isolated peptide consists of the amino acid sequence of SEQ ID NO:1.

9. The fusion peptide of claim 2, wherein the heterologous peptide is a granulocyte-macrophage colony-stimulating factor (GM-CSF).

10. A composition comprising the isolated peptide of claim 1 and a physiologically acceptable excipient.

11. A composition comprising the fusion peptide of claim 2 and a physiologically acceptable excipient.

12. The composition of claim 10, wherein the isolated peptide consists of the amino acid sequence of SEQ ID NO:1.

13. The composition of claim 11, wherein the isolated peptide consists of the amino acid sequence of SEQ ID NO:1.

14. The composition of claim 11, wherein the heterologous peptide is a granulocyte-macrophage colony-stimulating factor (GM-CSF).

15. The composition of claim 10, further comprising an antigen-presenting cell with the isolated peptide forming a complex with a major histocompatibility complex (MHC) molecule on the surface of the cell.

16. A method for detecting in a patient a T cell immune response specific to human prostatic acid phosphatase (PAP) protein, the method comprising the steps of (a) obtaining an antigen-presenting cell and a T cell from the patient; (b) contacting the antigen-presenting cell and the T cell with the isolated peptide of claim 1; and (c) detecting a T cell response, wherein the detection of a T cell response indicates the presence of a T cell immune response specific to the PAP protein in the patient.

17. The method of claim 16, wherein step (c) is performed by ELISPOT, proliferation assay, or flow cytometry.

18. The method of claim 16, wherein the isolated peptide consists of the amino acid sequence of SEQ ID NO:1.

* * * * *

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: residues 257-271 of human prostatic acid
      phosphatase (PAP), PAP epitope 257-271,
      Peptide #65, PAP-257-271

<400> SEQUENCE: 1

Arg Leu Gln Gly Gly Val Leu Val Asn Glu Ile Leu Asn His Met
1               5                   10                  15

<210> SEQ ID NO 2
<211> LENGTH: 21
<212> TYPE: PRT
<213> ORGANISM: Artificial Sequence
<220> FEATURE:
<223> OTHER INFORMATION: residues 254-274 of human prostatic acid
      phosphatase (PAP), 254-274 seqment

<400> SEQUENCE: 2

Glu Lys Ser Arg Leu Gln Gly Gly Val Leu Val Asn Glu Ile Leu Asn
1               5                   10                  15

His Met Lys Arg Ala
            20
```